United States Patent [19]
McDevitt

[11] Patent Number: 5,204,775
[45] Date of Patent: Apr. 20, 1993

[54] DEVICE FOR MAGNIFYING INDICIA PRINTED ON A CONTAINER

[75] Inventor: Timothy E. McDevitt, Clinton, Conn.

[73] Assignee: TT&B, Inc., Clinton, Conn.

[21] Appl. No.: 830,728

[22] Filed: Feb. 4, 1992

[51] Int. Cl.[5] ............................................. G02B 27/02
[52] U.S. Cl. .................................... 359/442; 359/436; 359/811
[58] Field of Search ............... 359/802, 803, 804, 805, 359/809, 810, 811, 815, 436, 440, 441, 442

[56] References Cited

U.S. PATENT DOCUMENTS

| | | | |
|---|---|---|---|
| 2,349,604 | 5/1944 | Barrows | 359/442 |
| 2,405,418 | 8/1946 | Fukal | 359/809 |
| 3,512,862 | 5/1970 | Yin | 359/436 |
| 3,762,799 | 10/1973 | Shapiro | 359/442 |
| 4,435,094 | 3/1984 | Shapiro | 359/442 |

Primary Examiner—Loha Ben
Attorney, Agent, or Firm—McCormick, Paulding & Huber

[57] ABSTRACT

A device for magnifying indicia printed on a container is provided. The device is designed to be releasably mounted to a prescription vial or other medication container to permit visually impaired individuals to read easily the label information relating to the safe and effective use of their medications. The device includes a magnifying medium which can be releasably attached to the container. Components are also provided for maintaining the medium in spaced relationship to the container to effect proper magnification of the indicia.

7 Claims, 2 Drawing Sheets

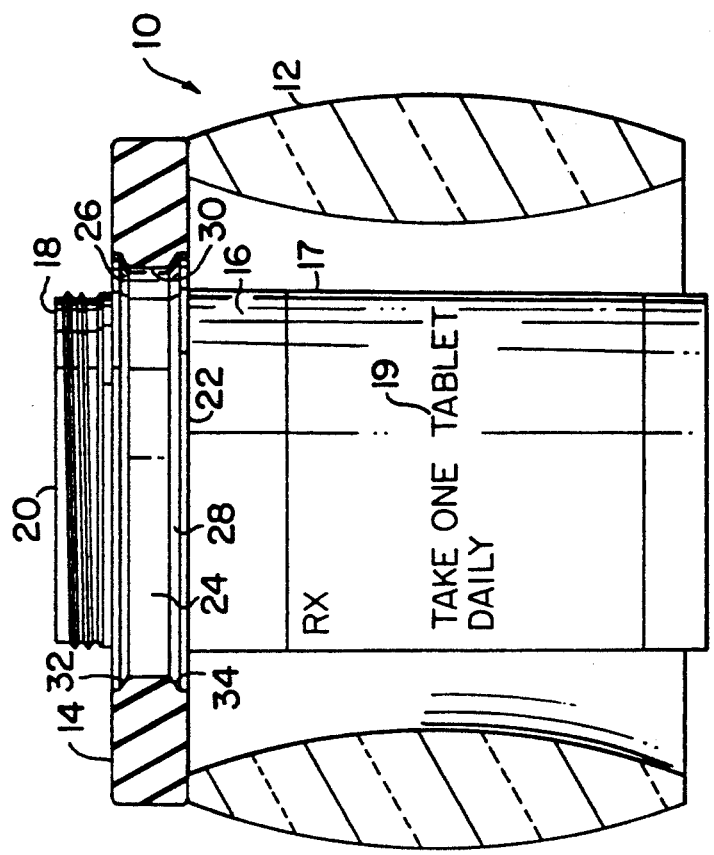
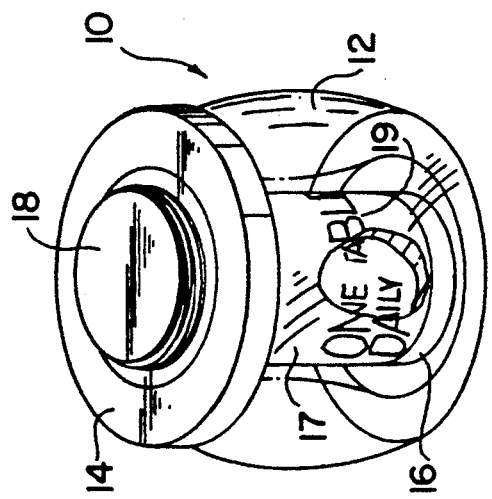

DEVICE FOR MAGNIFYING INDICIA PRINTED ON A CONTAINER

BACKGROUND OF THE INVENTION

The present invention relates to a magnifying device for containers bearing printed matter or other indicia which must be communicated to consumers. More particularly, the present invention provides a magnifying device for prescription vials and bottles that enables the visually impaired to easily read dosage directions and other label information pertinent to the safe and effective use of medications, especially prescription medications.

A substantial number of people who regularly use prescription and over the counter medications suffer from glaucoma, cataracts and other visual impairments. Unfortunately, this often makes it difficult for these individuals to read the label directions and safety warnings on their medications. Thus, when taking their medications, the visually impaired make an alarming number of errors in both dosage and dosage frequency. In addition, they frequently are not aware of label information concerning safety warnings, contra-indications and drug interactions.

Accordingly, it is an object of the invention to provide a device for prescription vials and bottles and other medication containers that permits visually impaired individuals to read easily the label information affixed to such containers.

It is a further object of the invention to provide such a device which can quickly an easily be attached to and removed from medication containers by pharmacists and consumers.

It is a still further object of this invention to provide such a device which can be repeatedly used on a wide variety of medication containers.

SUMMARY OF THE INVENTION

The present invention meets these and other objects by providing a device for magnifying indicia printed on a container, such as dosage information printed on the label of a prescription vial or bottle. The device includes a magnifying medium for magnifying the indicia and means for releasably attaching the magnifying medium to the container. The device further includes means for maintaining the magnifying medium in spaced relationship to the indicia to effect magnification thereof when the device is attached to the container.

In one preferred embodiment of the invention, the device comprises a bi-convex lens which completely surrounds the container and which is releasably mounted to the container. When mounted on the container, the lens is spaced a sufficient distance from the indicia to effect magnification thereof.

In another preferred embodiment of the invention, the device comprises a flexible fastener which is formed with a window opening. The fastener is placed at least partially around the container with the window opening overlying the indicia carried by the container. The window opening is covered with a substantially flat, flexible lens, and means are provided for maintaining the lens in spaced relationship to the indicia to effect magnification thereof. Means are also provided for releasably attaching the fastener to the container.

BRIEF DESCRIPTION OF THE DRAWINGS

FIG. 1 is a partially cut away perspective view of a device made according to the invention attached to a prescription vial.

FIG. 2 is a sectional view of the embodiment of the invention shown in FIG. 1.

DETAILED DESCRIPTION OF THE INVENTION

Figure 4:
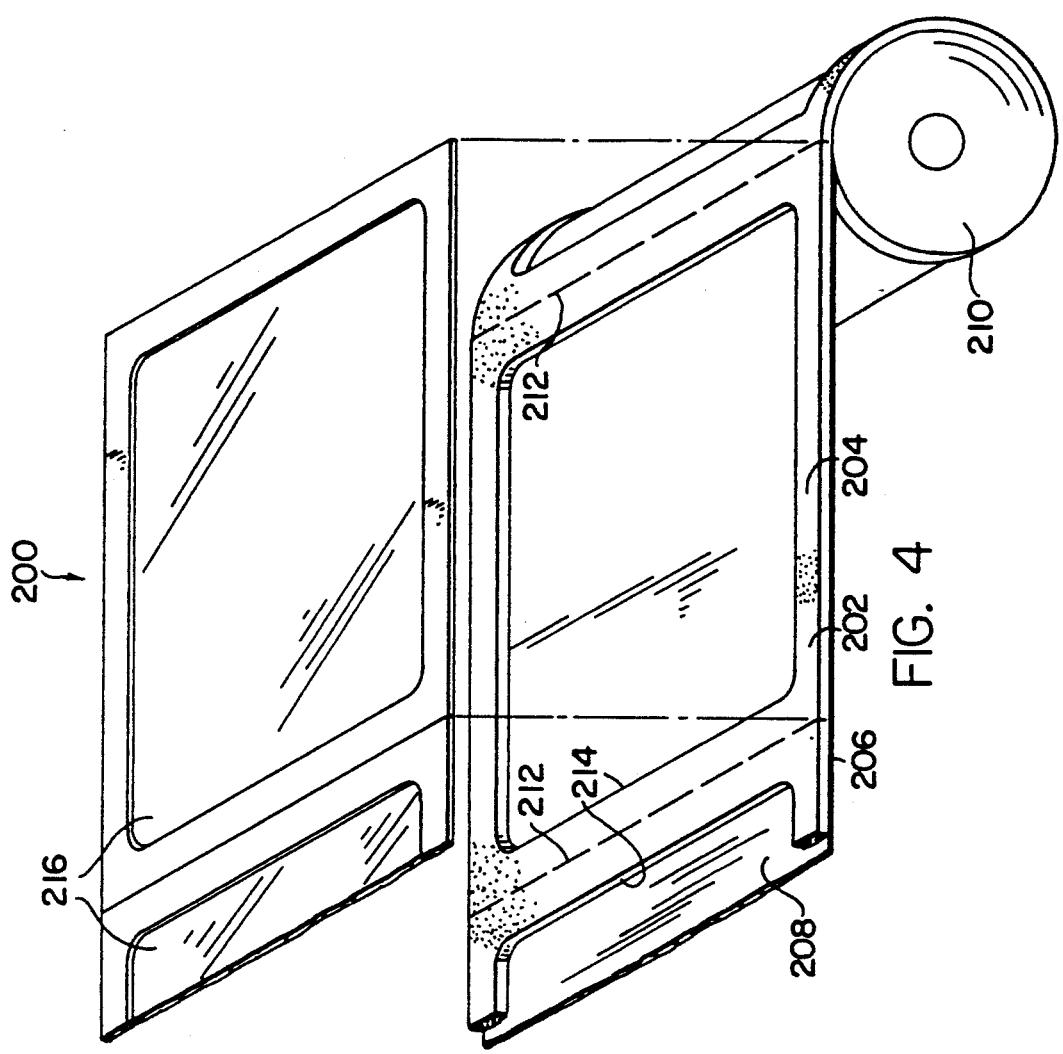
FIG. 4 is a partially exploded perspective view of a third embodiment of the invention.

FIG. 1 illustrates a preferred embodiment of a device made according to the present invention. The device 10 includes a bi-convex lens 12 carried by an annular collar 14. The device is shown surrounding a prescription vial 16 in assembly with a cap 18. The vial 16 has a label 17 affixed thereto. As shown in FIG. 1, the lens 12 is spaced by the collar 14 a sufficient distance from the label to effect magnification of the printed matter 19 carried by the label. Those skilled in the art will recognize that the distance which the lens 12 must be spaced from the vial 16 depends on a number of factors including the magnification required, the index of refraction of the lens, the inside and outside radii of the lens and the lens' focal length.

The vial and cap assembly is of a type commonly used for dispensing prescription medications. The vial 16 is designed with bayonet type latches (not shown) for accepting a standard child safety closure. The vial also includes threads (not shown) for receiving a screw-type cap for those individuals who prefer non-safety closures on their medications. The cap 18 is designed to fit a number of different size vials and is reversible. One end 20 of the cap is threaded so that it can simply be screwed into the vial 16. The opposite end 22 of the cap (see FIG. 2) includes bayonet latches (not shown) which engage those on the bottle to form a safety closure.

Referring now to FIG. 2, the collar 14 and the end 22 of the cap are adapted for snap engagement so that the device 10 can simply be pressed onto and pulled off of the vial/cap assembly as required. The end 22 of the cap 18 has a groove 24 formed therein which forms associated shoulders 26, 28. The collar 14 is made from a resilient, preferably elastomeric, material and is formed with an annular bead 30 having associated, substantially symmetrical cam surfaces 32, 34. Since the collar is resilient, it will expand when, for example, cam surface 32 is pressed against shoulder 26. This allows bead 30 to snap into groove 24 to engage the device 10 with the cap. Similarly, the device 10 can be removed from the vial/cap assembly by pulling the device downwardly toward the bottom of vial 16 to force cam surface 34 against shoulder 28 and expand collar 14 so that bead 30 snaps free of groove 24.

Accordingly, the device can be easily attached or detached from the vial/cap assembly. This allows a pharmacist, for example, to attach the device to a vial/cap assembly at the time a prescription is filled. Alternatively, patients can obtain the device on their own and attach it to their prescription vials or other medication containers at the time they take their medications. Since the cap 18 is designed to fit vials of different sizes, patients can repeatedly remove and attach the device for use with several different medication containers.

Those skilled in the art will easily recognize that the present invention is in no way limited by the described embodiment. For example, the lens 12 need not completely surround the vial; the lens need only extend over that portion of the vial's surface to which the label is affixed. Further the collar 14 need not be completely annular but could, for example, be formed as a split ring. Still further, the lens and collar can be formed as an integral piece or as separate pieces adhered together.

Figure 3:
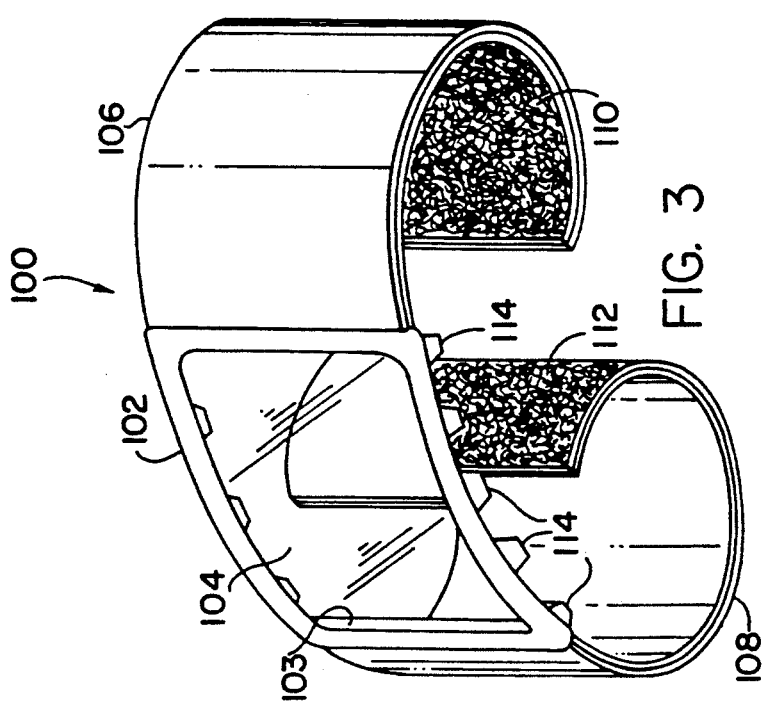
FIG. 3 is a perspective view of a second embodiment of the present invention.

FIG. 3 illustrates an alternate embodiment of the present invention. As shown in FIG. 3, the device 100 includes a frame 102 which defines a window opening 103. The frame is contoured to substantially conform to the curved surface of a prescription vial or other medication container. The opening defined by the frame is covered by a substantially flat, flexible lens 104. The device 100 further includes a pair of straps 106, 108. Each of the straps is connected at one end to the frame 102, and the free ends of the straps are provided with a separable closure 110, 112, such as a "VELCRO" closure. Thus, the device 100 can be affixed to a medication container by placing the frame over that portion of the container carrying the label information and then tightly wrapping the straps around the container until their free ends overlap. Spacing elements 114 are provided to properly space the lens 104 from the surface of the container to effect magnification of the label information when the device is affixed to the container.

Still another alternate embodiment of the present invention is shown in FIG. 4. The device 200 comprises a strip 202 of flexible foam coated on its upper 204 and lower 206 surfaces with a pressure sensitive release adhesive. The strip 202 is mounted on a release backing 208 and is supplied in a roll 210 formed from a large number of such strips divided by perforations 212 to facilitate removal of individual strips. The strip 202 has a window opening 214 formed therein. The device 200 further includes a substantially flat, flexible lens 216 releasably mounted on the upper surface 204 of the strip by the adhesive. The lens 216 overlies at least a portion of the strip and forms a closure for the window opening 214. The device is positioned on a medication container with the window opening overlying the label affixed to the container and is releasably attached to the container by the pressure sensitive adhesive coating the lower surface 206 of the strip. The foam forming the strip is provided in a sufficient thickness to space the lens 216 from the container's surface so that the label information is properly magnified.

While preferred embodiments have been shown and described, various modifications and substitutions may be made without departing from the spirit and scope of the invention. Accordingly, it is to be understood that the present invention has been described by way of example and not by limitation.

I claim:

1. A device for magnifying indicia printed on a container, wherein said container is in assembly with a cap member, said device comprising:
   a bi-convex lens at least partially surrounding said container for magnifying said indicia;
   means for releasably attaching said device to said cap member, and
   means for maintaining said bi-convex lens in spaced relationship to said indicia to effect magnification thereof when said device is attached to said container.

2. The device of claim 1 further comprising an annular collar, wherein said bi-convex lens is carried by said collar and said collar is maintained in snap engagement with said cap member.

3. A device for magnifying indicia printed on a container, said device comprising:
   a flexible fastener having a window opening therethrough, said fastener adapted to releasably attach said device to said container;
   a substantially flat, flexible lens overlying at least a portion of said fastener and forming a closure for said window.

4. The device of claim 3 wherein said fastener is a strip of foam coated on at least one surface with a release adhesive to releasably attach said device to said container, said foam having a thickness sufficient to maintain said lens in spaced relationship to said container to effect magnification of said indicia.

5. The device of claim 3 wherein said fastener comprises a frame member defining said window opening and a pair of bands, each of said bands connected at one end to said frame member, wherein the free ends of said bands are provided with a separable closure for releasably attaching said device to said container.

6. The device of claim 5 further comprising at least one spacing element associated with said frame for maintaining said lens in spaced relationship to said container to effect magnification of said indicia.

7. A device for magnifying indicia printed on a container including a cap, said device comprising:
   a bi-convex lens at least partially surrounding said container for magnifying said indicia when said device is attached to said container;
   an annular collar for maintaining said device in snap engagement with said container, and
   means for maintaining said lens in spaced relationship to said indicia to effect magnification thereof when said device is attached to said container.

* * * * *